(12) United States Patent
Virnich et al.

(10) Patent No.: US 8,957,689 B2
(45) Date of Patent: Feb. 17, 2015

(54) CAPACITIVE OCCUPANT DETECTION SYSTEM

(75) Inventors: Michael Virnich, Korlingen (DE); David Hoyer, Ayl (DE); Martin Thinnes, Trierweiler (DE)

(73) Assignee: IEE International Electronics & Engineering S.A., Luxembourg (LU)

( * ) Notice: Subject to any disclaimer, the term of this patent is extended or adjusted under 35 U.S.C. 154(b) by 134 days.

(21) Appl. No.: 13/823,394

(22) PCT Filed: Sep. 16, 2011

(86) PCT No.: PCT/EP2011/066055
§ 371 (c)(1),
(2), (4) Date: Apr. 16, 2013

(87) PCT Pub. No.: WO2012/038325
PCT Pub. Date: Mar. 29, 2012

(65) Prior Publication Data
US 2013/0207676 A1    Aug. 15, 2013

(30) Foreign Application Priority Data

Sep. 23, 2010 (LU) ............................. 91739

(51) Int. Cl.
*G01R 27/26* (2006.01)
*G08B 21/00* (2006.01)
(Continued)

(52) U.S. Cl.
CPC .......... *G01R 27/2605* (2013.01); *G01N 27/226* (2013.01); *G01N 27/22* (2013.01); *B60N 2/002* (2013.01); *B60N 2/5685* (2013.01); *B60R 21/015* (2013.01); *G01V 3/088* (2013.01)
USPC ............ 324/684; 324/686; 324/688; 340/667

(58) Field of Classification Search
CPC .... B60N 2/002; B60N 2/5685; B60R 21/015; G01R 27/2605; G01V 3/088; G01L 9/12; G01N 27/22; G01N 27/221; G01N 27/223; G01N 27/226; G01N 27/227; G01N 27/228

USPC ......... 324/684, 658, 649, 600, 688, 686, 679, 324/672, 671, 669, 664, 663, 662, 661, 324/660; 340/667, 666, 665
See application file for complete search history.

(56) References Cited

U.S. PATENT DOCUMENTS 6,025,726 A    2/2000  Gershenfeld et al.
6,960,841 B2 *  11/2005  Saitou et al. ................. 307/10.1
(Continued)

FOREIGN PATENT DOCUMENTS

| EP | 2085263 A1 | 1/2008 |
| EP | 2090460 A1 | 2/2008 |
| WO | 0192900 A1 | 12/2001 |

OTHER PUBLICATIONS

International Search Report for corresponding application PCT/EP2011/066055 filed Sep. 16, 2011; Mail date Dec. 12, 2011.
(Continued)

*Primary Examiner* — Hoai-An D Nguyen
(74) *Attorney, Agent, or Firm* — Cantor Colburn LLP (57) ABSTRACT

A capacitive occupant detection system comprises at least one antenna electrode to be arranged in a seat and an evaluation unit operatively coupled to said at least one antenna electrode, said evaluation unit being configured for applying, during operation, an alternating voltage signal to said antenna electrode and for detecting an amplitude and/or phase of a displacement current flowing from said antenna electrode towards ground. According to the invention said antenna electrode comprises an antenna electrode conductor and at least one dedicated ground electrode, said ground electrode being arranged at a predetermined distance of said antenna electrode conductor and extending along said antenna electrode conductor.

10 Claims, 6 Drawing Sheets

(51) Int. Cl.
   *G01N 27/22*    (2006.01)
   *B60N 2/00*     (2006.01)
   *B60N 2/56*     (2006.01)
   *B60R 21/015*   (2006.01)
   *G01V 3/08*     (2006.01)

(56) References Cited

U.S. PATENT DOCUMENTS

| | | | |
|---|---|---|---|
| 7,656,169 B2 * | 2/2010 | Scheckenbach et al. | 324/679 |
| 7,701,338 B2 * | 4/2010 | Kamizono et al. | 340/561 |
| 8,330,609 B2 * | 12/2012 | Miyamori et al. | 340/667 |
| 8,519,725 B2 * | 8/2013 | Uno et al. | 324/663 |
| 8,698,511 B2 * | 4/2014 | Wendt et al. | 324/679 |
| 2010/0277186 A1 * | 11/2010 | Bieck et al. | 324/674 |
| 2013/0021045 A1 * | 1/2013 | Virnich et al. | 324/686 |
| 2013/0092677 A1 * | 4/2013 | Virnich et al. | 219/204 |
| 2013/0098890 A1 * | 4/2013 | Virnich et al. | 219/204 |

OTHER PUBLICATIONS

J.R. Smith, "Electric Field Sensing for Graphical Interfaces", IEEE Computer Graphics and Applications; published in Computer Graphics I/O Devices, Issue May/Jun. 1998, pp. 54-60.

Written Opinion for corresponding application PCT/EP2011/066055 filed Sep. 16, 2011; Mail date Dec. 12, 2011.

* cited by examiner

CAPACITIVE OCCUPANT DETECTION SYSTEM

TECHNICAL FIELD

The present invention generally relates to the field of capacitive occupant detection systems e.g. to be used in the control of the deployment of secondary restraint systems of an automotive vehicle such as airbags, seat belt pretensioners and the like. The invention more particularly relates to capacitive occupant detection systems operating in the so called loading mode and for which a sensing electrode is arranged or assembled in close proximity to a seat heating unit in a vehicle seat.

BACKGROUND ART

Capacitive measurement and/or detection systems have a wide range of applications, and are among others widely used for the detection of the presence and/or the position of conductive body in the vicinity of an electrode of the system. A capacitive sensor, called by some electric field sensor or proximity sensor, designates a sensor, which generates a signal responsive to the influence of what is being sensed (a person, a part of a person's body, a pet, an object, etc.) upon an electric field. A capacitive sensor generally comprises at least one antenna electrode, to which is applied an oscillating electric signal and which thereupon emits an electric field into a region of space proximate to the antenna electrode, while the sensor is operating. The sensor comprises at least one sensing electrode—which could comprise the one or more antenna electrodes themselves—at which the influence of an object or living being on the electric field is detected.

The technical paper entitled "Electric Field Sensing for Graphical Interfaces" by J. R. Smith, published in Computer Graphics I/O Devices, Issue May/June 1998, pp 54-60 describes the concept of electric field sensing as used for making non-contact three-dimensional position measurements, and more particularly for sensing the position of a human hand for purposes of providing three dimensional positional inputs to a computer. Within the general concept of capacitive sensing, the author distinguishes between distinct mechanisms he refers to as "loading mode", "shunt mode", and "transmit mode" which correspond to various possible electric current pathways. In the "loading mode", an oscillating voltage signal is applied to a transmit electrode, which builds up an oscillating electric field to ground. The object to be sensed modifies the capacitance between the transmit electrode and ground. In the "shunt mode", which is alternatively referred to as "coupling mode", an oscillating voltage signal is applied to the transmit electrode, building up an electric field to a receive electrode, and the displacement current induced at the receive electrode is measured, whereby the displacement current may be modified by the body being sensed. In the "transmit mode", the transmit electrode is put in contact with the user's body, which then becomes a transmitter relative to a receiver, either by direct electrical connection or via capacitive coupling.

The capacitive coupling is generally determined by applying an alternating voltage signal to a capacitive antenna electrode and by measuring the current flowing from said antenna electrode either towards ground (in the loading mode) or into the second electrode (receiving electrode) in case of the coupling mode. This current is usually measured by means of a transimpedance amplifier, which is connected to the sensing electrode and which converts a current flowing into said sensing electrode into a voltage, which is proportional to the current flowing into the electrode.

While the above measurement principle generally leads to very useful results, it is clear that problems may arise in the vicinity of grounded structures (e.g. seat heaters in a vehicle seat). A seat heater comprises a heating element, which is typically a low-resistance conductor (in the form of a wire, cable, conductive trace printed on an insulating substrate, or the like) for being arranged under the seat cover.

The base capacitance measured between the sensing electrode of a capacitive occupant detection system and the reference electrode (car body) increases in close vicinity of a seat heater structure especially for systems without guard/shield electrode. This is due to the additional capacitive coupling between the sensing electrode and the seat heater structure, which by itself has a low impedance connection to the reference electrode (car body ground). Accordingly it is normally not possible to clearly separate the capacitance influence of the seat heater structure from the influence of the remaining car body since for example the seat heater structure is usually a separate unit. As a further effect, this capacitance is subject to tolerances due to (assembly-related) variations in distance between sensing electrode and seat heater structure, due to ageing effects of the composite material between the sense electrode and the seat heater, as well as modifications of physical parameters of said composite material (e.g. permittivity). This increased capacitance and the related tolerances affect the useful dynamics of a connected measurement system and limit the accuracy of decisional thresholds and the robustness of these thresholds. Finally as there is also a capacitive coupling between the sensing electrode and the seat frame, said seat frame's grounding state needs to be also controlled to avoid variance in the capacitive load.

In the current state of the art, the seat heater influence and the seat frame influence might be reduced by the use of a guard/shield electrode between the sense electrode and the seat heater or by active functional coupling with a seat heater electronics module which is controlled by the capacitive measurement system. These current implementations increase system cost (additional large-area guard electrode) and/or complexity (interaction with seat heater module).

BRIEF SUMMARY

The invention proposes a capacitive sensing system with seat heater and seat frame influence compensation.

A capacitive occupant detection system comprises at least one antenna electrode to be arranged in a seat and an evaluation unit operatively coupled to said at least one antenna electrode, said evaluation unit being configured for applying, during operation, an alternating voltage signal to said antenna electrode and for detecting an amplitude and/or phase of a displacement current flowing from said antenna electrode towards ground. According to the invention said antenna electrode comprises an antenna electrode conductor and at least one dedicated ground electrode, said ground electrode being arranged at a predetermined distance of said antenna electrode conductor and extending along said antenna electrode conductor.

Existing combinations of capacitive sensing systems and seat heaters often feature parallel or quasi-parallel sensing electrodes/seat heater wire design. This, on the one hand, generates a relatively high constant capacitive offset in the capacitive sensing system and reduces thus the relative measurement dynamics. On the other hand, as this capacitive offset depends on the distance between seat heater and sensing electrode, parallel or quasi-parallel sensing electrodes/ seat heater wire design is very sensitive against assembly/production tolerances and needs to be costly controlled. According to the present invention, the influence of the seat frame and the seat heater on the capacitive offset in the sensing system is reduced by establishing a known and defined capacitive coupling between the sensing electrode and vehicle GND, which, in parallel, causes the coupling between sensing electrode and seat frame to decrease.

It should be noted that in the context of the present invention, the expression parallelism should be understood largely to cover not only straight conductors extending in a parallel manner but also differently shaped conductors, which extend one along the other. In fact the heater conductor and the antenna electrode conductor have preferably meandering shapes extending over a major part of the seating surface of the seat. In the context of such meandering conductors, the expression parallelism or quasi-parallelism is meant to cover two meander-shaped conductors extending along each other. Likewise the basic orientation of the heater conductor and the basic orientation of the antenna electrode conductor have to be understood to designate the global orientation of the conductors, which in a meandering shape would normally be understood to be equal to the direction of the main segments or regions forming the meandering shape.

Figure 5:
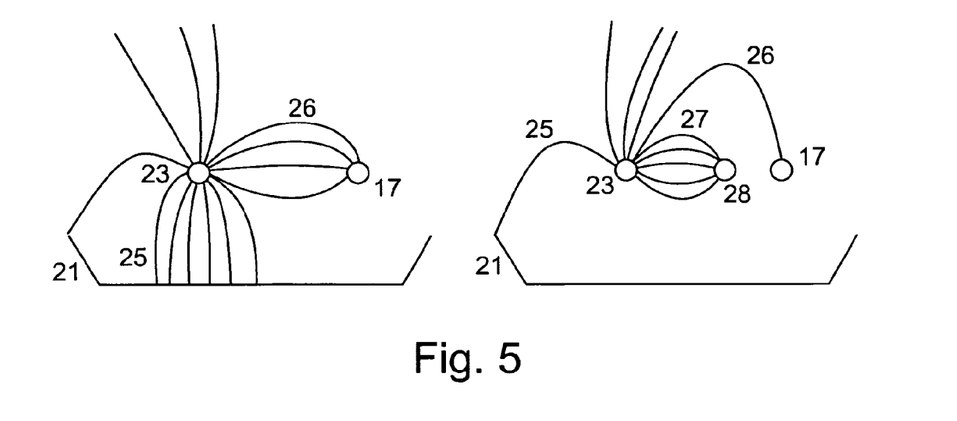
FIG. 5 shows the effect of a dedicated ground electrode to the electrical field.

Adding a defined capacitive coupling path to GND according to FIG. 5 has the benefit that the capacitive offset in the sensing system remains virtually constant. A drawback is that the capacitive offset usually increases, leading to a reduced measurement dynamics. In a preferred embodiment of the invention, the evaluation unit therefore further comprises circuitry for compensating the capacitive current flowing from said antenna electrode conductor to said at least one dedicated ground electrode. As the current flowing from the sensing electrode to the dedicated ground electrode represents a constant offset in the overall current flowing into the capacitive electrode and can be determined by calculation without measuring it, it can be subtracted from the overall current which results in a differential current still carrying the information about the change in occupancy status. Said differential current can be taken for evaluation in the sensing system.

It will be appreciated that the present invention is especially useful in an assembly of a seat heater and a capacitive occupant detection system. The seat heater comprises at least one heater conductor to be arranged in a seat. In this case, the said seat heater and a capacitive occupant detection system are preferably arranged in said seat in such a way, that said dedicated ground electrode is arranged between said heater conductor and said antenna electrode conductor. In fact, if one or more GND electrodes are added in close proximity to the sensing electrode, e. g. between sensing electrode and seat heater wiring, the electrical field which develops around the sensing electrode is of completely different shape than without the ground electrode, leading to a smaller capacitive coupling between the sensing electrode and the seat heater. In that case, there is virtually no impact of a seat heater interruption or assembly tolerances between seat heater and the sensing electrode on the classification performance of the sensing system.

It will further be noted that said heater conductor and/or said antenna electrode conductor and/or said ground electrode may comprise a conductive wire and/or a conductive trace applied on a carrier material. The skilled person will further appreciate that the heater conductor and the antenna electrode conductor may be arranged on a common carrier material or on individual carrier materials, and that the sensing electrode may be arranged above the heater conductor of vice versa. Finally it will be noted that the antenna electrode conductor is preferably loop shaped with both the first and the second end of said loop being connected to the evaluation unit so that the integrity of the electrode conductor is checkable by known means.

BRIEF DESCRIPTION OF THE DRAWINGS

Preferred embodiments of the invention will now be described, by way of example, with reference to the accompanying drawings in which:

FIG. 6.1-6.3 shows a schematic layout of a seat heater (6.1), a schematic layout of a sensing and GND electrode (6.2) and the assembled layout of the seat heater and the sensing and GND electrode (6.3);

DESCRIPTION OF PREFERRED EMBODIMENTS

Figure 1:
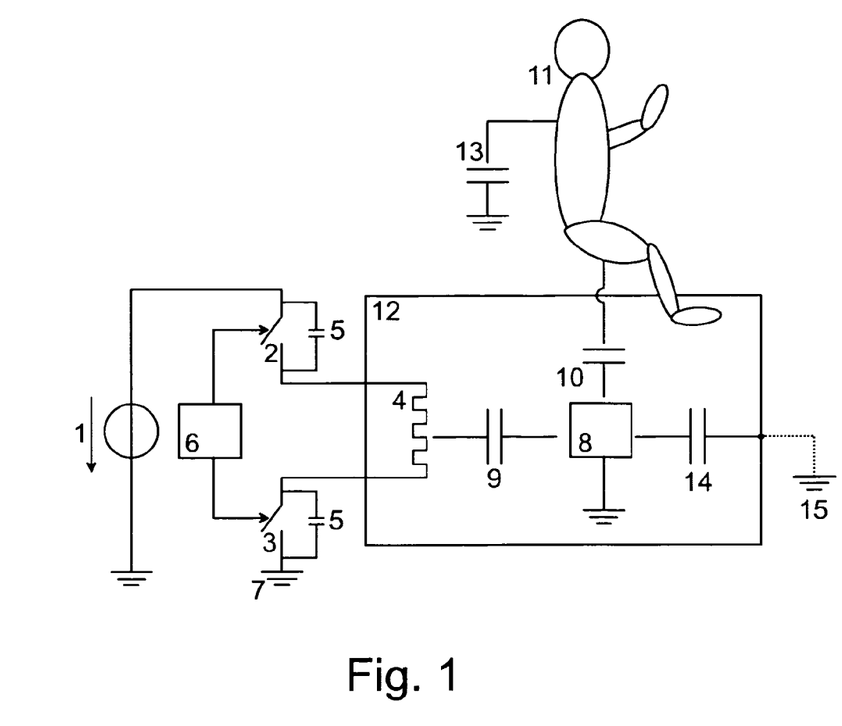
FIG. 1 shows a possible embodiment of a capacitive sensing system.

FIG. 1 shows an exemplified seat heater connection circuitry and capacitive measurement system. The different reference numerals denote the following features: 1 is the vehicle's power supply (battery voltage); 2 is a high side power switch; 3 is the low side power switch; 4 is the seat heater; 5 is the parasitic capacitance of the high side/low side power switch; 6 is the seat heater control unit; 7 is the vehicle's GND; 8 capacitive sensing system; 9 capacitive coupling between seat heater and sensing electrode; 10 capacitive coupling between sensing electrode and passenger; 11 is the passenger; 12 is the seat frame; 13 is the passenger's capacitance to GND; 14 capacitive coupling between sensing electrode and seat frame; 15 is the grounding connection of the seat frame.

Today's automotive capacitive sensing systems used to activate/de-activate the airbag in case of a crash use either the seat heater, a separate sensing electrode or a shielded electrode as sensing element. In any case, the seat heater has to be AC-decoupled from vehicle's ground GND, since, even if the seat heater is not switched ON, it is coupled to GND from an AC point of view via the power switches parasitic capacitances. FIG. 1 features a typical seat heater connection circuitry together with a separate capacitive sensing system usually assembled in the passenger seat of a vehicle. Typically, the grounding state 15 of the metallic seat frame 12 is not well defined.

The seat heater 4 is connected to the vehicle's power via either a high side switch 2 or a low side switch 3 or both. These switches are controlled by the seat heater control unit 6 in order to adjust the correct seat temperature. Normally, the switches are field effect transistors, but they can also be mechanical or electro-mechanical switches.

The parasitic capacitances 5 cause the seat heater to be coupled to the vehicle's GND 7, even if the seat heater is not switched ON. For this reason, via the coupling capacitance 9, the capacitive sensing unit 8 measures a capacitive offset depending on said coupling capacitance 9 and the parasitic capacitances 5. In addition, the capacitive offset is increased by the coupling 14 between sensing electrode and seat frame 12.

If this capacitive offset varies due to e. g. an interrupted seat heater 4 or a undefined grounding connection 15 of the seat frame 12, the ability of the system to detect the passenger 11 sitting on the passenger seat by determination of the series capacitance formed by capacitor 10 and 13 degrades.

Said series capacitance is used to differentiate between persons sitting on the seat and child seat, for which the airbag deployment shall be suppressed in case of a crash. Low values of the series capacitance cause the sensing system to decide that the passenger seat is empty or occupied by a CRS, which will lead to a deactivation of the airbag in both cases. High values of the series capacitance cause the sensing system to decide that a person is sitting on the passenger seat, which leads to an activation of the airbag to deploy in case of a crash and, thus, protecting the passenger.

Figure 2:
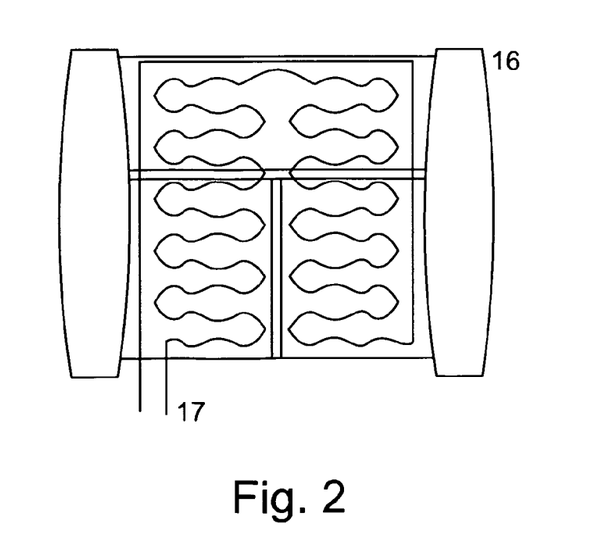
FIG. 2 shows a top view of a vehicle seat equipped with a seat heater.

FIG. 2 shows a top view of a vehicle seat equipped with a seat heater. Reference numeral 16 denotes the vehicle seat and reference numeral 17 a (wire based) seat heater. Today's capacitive sensing systems use either the seat heater as sense electrode or a separate shielded or un-shielded sensing electrode, placed above the seat heater or integrated together with the seat heater on the same carrier material. Especially the performance of realizations with un-shielded separate electrodes degrades due to the high capacitive coupling between sensing electrode and seat heater.

Figure 3:
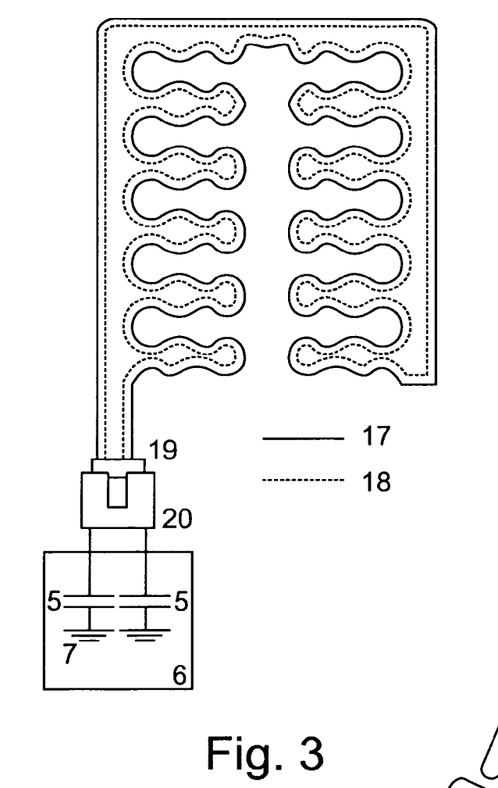
FIG. 3 shows a schematic layout of a seat heater electrical connection.

FIG. 3 shows a schematic layout of a seat heater electrical connection. The different reference numerals in FIG. 3 denote the following features: 5 is the parasitic coupling of the power switches inside the seat heater control unit; 6 is the seat heater control unit; 7 is the vehicle's GND; 17 is the (wire based) seat heater; 18 is the capacitive system's sensing electrode; 19 is the seat heater connector; 20 is the socket for the seat heater connector. FIG. 3 shows an example of an embodiment of a capacitive sensing system with an un-shielded electrode. Both seat heater 17 and sensing electrode 18 can be, but must not be, integrated on one carrier. Since the sensing electrode's wiring is basically hold in parallel to the seat heater's wiring, there is a high capacitive coupling between seat heater and sensing electrode, which causes a high capacitive offset in the sensing system. If this offset varies due to e. g. assembly tolerances between sensing electrode and seat heater or an unplugged seat heater connector 19, misclassification might be possible.

Figure 4:
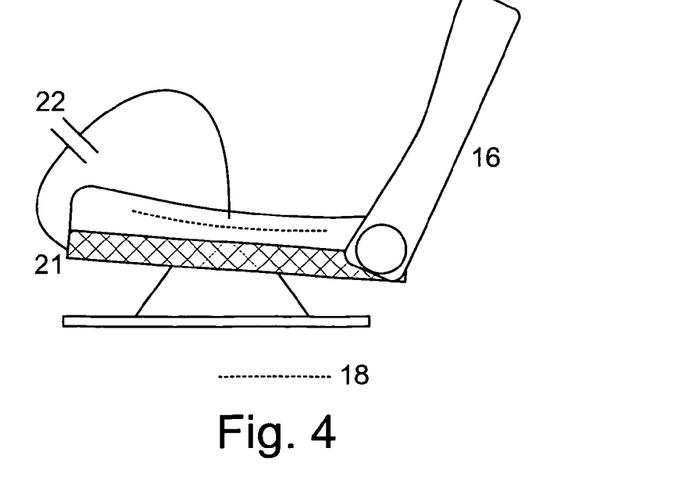
FIG. 4 schematically illustrates the capacitive coupling between sensing system and seat frame.

In addition to the coupling to the seat heater, there is a capacitive coupling 22 between sensing electrode 18 and the seat frame 21 of the seat 16, see FIG. 4. Depending on the grounding state of said seat frame 21, the capacitive offset in the sensing system might vary, increasing the probability for a misclassification.

The influence of the seat frame 21 or the seat heater 17 on the capacitive offset in the sensing system can be reduced by establishing a known and defined capacitive coupling between the sensing electrode and vehicle GND, which, in parallel, causes the coupling between sensing electrode and seat frame to decrease.

FIG. 5 shows the effect of a dedicated ground electrode to the electrical field. Without the GND electrode 28, there is a capacitive coupling 25 and 26 between sensing electrode 23 and seat frame 21 and sensing electrode 23 and seat heater 17. The grounding states of the seat heater 17 and the seat pan 21 are subject to variations, increasing the risk for misclassification by the sensing system.

If one or more GND electrodes 28 are added in close proximity to the sensing electrode 23, e. g. between sensing electrode and seat heater wiring, the electrical field which develops is of completely different shape, leading to a smaller capacitive coupling 25 between sensing electrode 23 and seat frame 21 and a smaller capacitive coupling 26 between sensing electrode 23 and seat heater 17.

In that case, variations of the seat frame's grounding state can be virtually neglected. In addition, there is virtually no impact of a seat heater interruption or assembly tolerances between seat heater and the sensing electrode on the classification performance of the sensing system.

Since the remaining capacitive offset in the sensing system is caused by the capacitive coupling 27 between sensing electrode 23 and GND electrode 28, there is virtually no change in said offset, as said coupling 27 can be well controlled, e. g. when sensing electrode 23 and GND electrode 28 are realized on the same carrier material.

Figure 61:
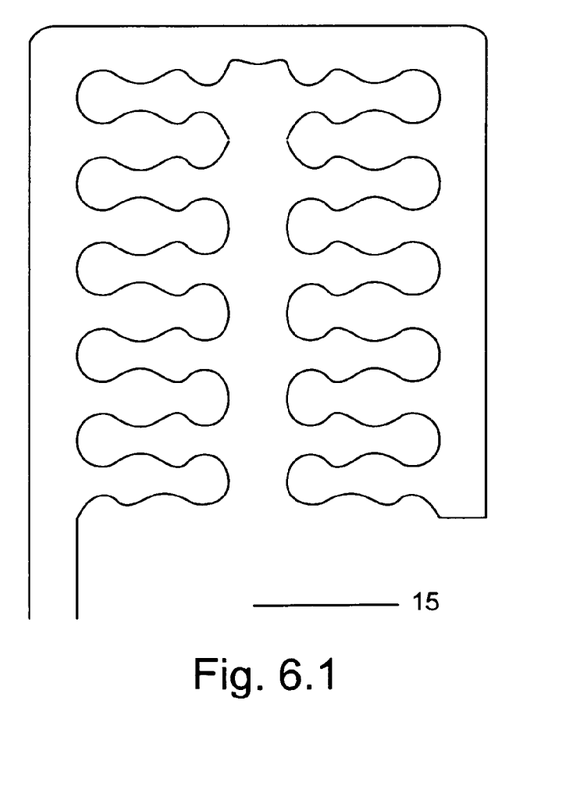
Figure 62:
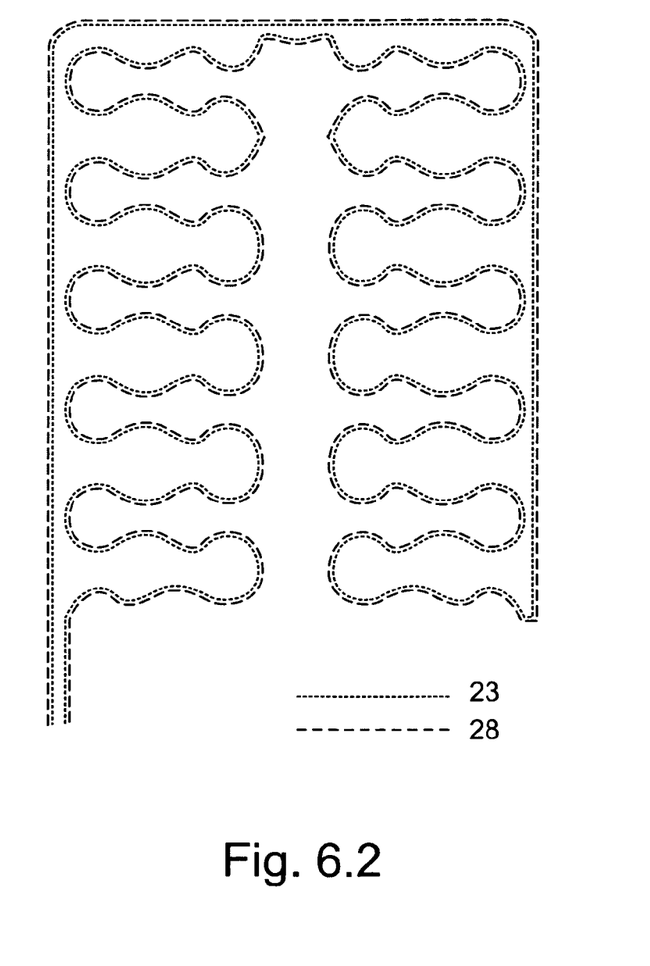
Figure 63:
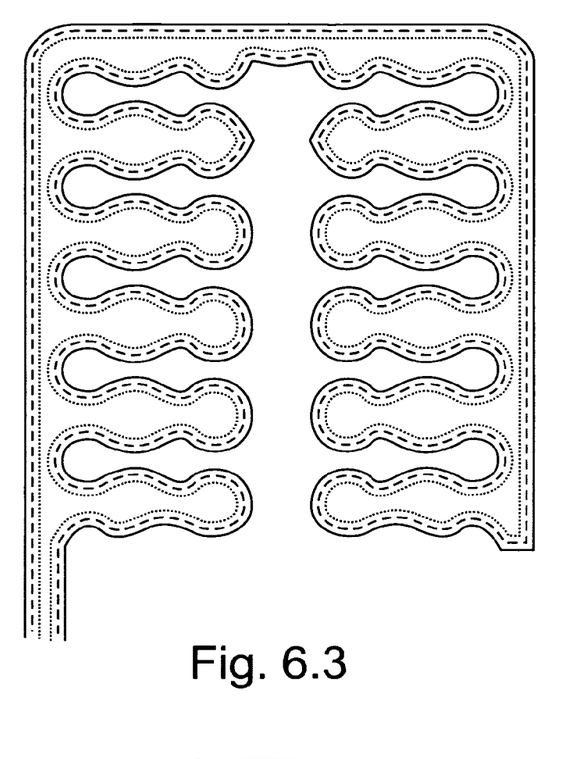

FIG. 6 shows a schematic layout of a seat heater (6.1), a schematic layout of a sensing and GND electrode (6.2) and the assembled layout of 6.1 and 6.2 (in 6.3). The GND electrode 28 is designed in such a way that, if assembled together with a seat heater 15 in a passenger seat, it virtually prevents capacitive coupling between sensing electrode 23 and seat heater 15. At the same time, the coupling between sensing electrode and seat frame can be virtually neglected. As a consequence, there is no need to diagnose the seat heater for interruption or to add a galvanic GND connection to the seat frame to realize a defined grounding status. Seat heater 15, sensing electrode 23 and GND electrode 28 can be, but most not be, arranged on one common carrier material.

Adding a defined capacitive coupling path to GND according to FIG. 5 has the benefit that the capacitive offset in the sensing system remains virtually constant. A drawback is that the capacitive offset usually increases, leading to a reduced measurement dynamics. In the following, a measure to avoid said drawback is explained with reference to FIG. 7, which shows the changed coupling situation due to added GND electrode, and FIG. 8, which illustrates a schematic layout of a constant capacitive offset compensation circuit in the sensing system.

Figure 7:
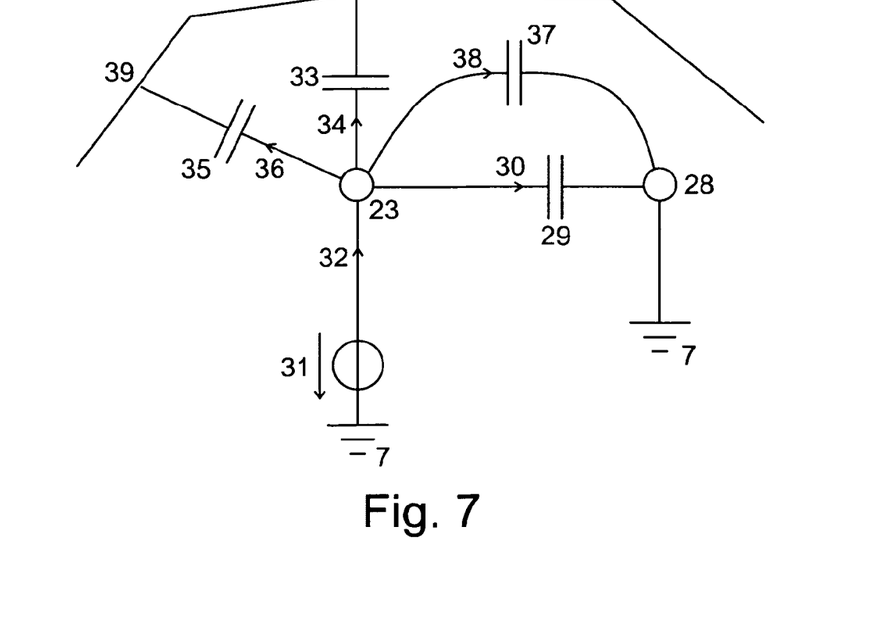
FIG. 7 shows the changed coupling situation due to added GND electrode.

Referring to FIG. 7, the different reference numerals denote the following features or elements: 7 is the vehicle's GND; 23 is the sensing electrode (vertical cut); 28 is a GND electrode (vertical cut, GND potential); 29 is the null capacitance between sensing electrode and GND electrode; 30 is the null current flowing from sensing to GND electrode; 31 is the AC voltage applied to the sensing electrode; 32 is the current flowing into the sensing electrode; 33 is the null capacitance between sensing electrode and vehicle chassis/seat frame; 34 is the null current flowing from sensing electrode to vehicle chassis/seat frame; 35 is the capacitance between sensing electrode and vehicle chassis caused by occupancy/environmental influences; 36 is the capacitive current through 35; 37 is the capacitance between sensing electrode and GND electrode caused by occupancy/environmental influences; 38 is the capacitive current through 37; 39 is the vehicle chassis on GND potential.

The capacitive sensing system applies the voltage 31 to the sensing electrode 23. The capacitive current 32 is evaluated by the sensing system in amplitude and/or phase angle in relation to the amplitude/phase angle of the applied AC voltage 31.

In an 'empty seat' condition, i.e. where the seat is neither occupied by a person nor by a Child Restraint Seat, said current 32 flowing into the sensing electrode splits up into a null current 30 flowing to the GND electrode 28 and a null current 34 flowing to the vehicle chassis/seat frame. Especially the null current 30 can reach high values and can be calculated out of the known AC voltage 32, the frequency of the AC voltage and the capacitance 29 between sensing electrode 23 and GND electrode 28, since latter capacitance is known and well defined by the geometry of sensing electrode 23 and GND electrode 28.

Due to a change in the occupancy situation or due to environmental influences like water on the passenger seat, current 32 changes in amplitude and phase angle in relation to the applied AC voltage 31. In FIG. 7, this is indicated by the capacitances 35 and 37. The currents 36 and 38 through said capacitances contain all necessary information about the changed occupancy situation and should be taken for evaluation.

Thus, as current 30 represents a constant offset in current 32 and can be determined by calculation without measuring it, it can be subtracted from current 32 which results in a differential current still carrying the information about the change in occupancy status. Said differential current can be taken for evaluation in the sensing system. Since only the remaining virtually constant offset in the differential current is due to the very low current 34 flowing through capacitance 33 between sensing electrode 23 and vehicle chassis 39, the measurement dynamics of the sensing system has increased.

Said current 34 can be compensated using the same principle if capacitance 33 is virtually constant, leading to a further increase of the measurement offset.

Figure 8:
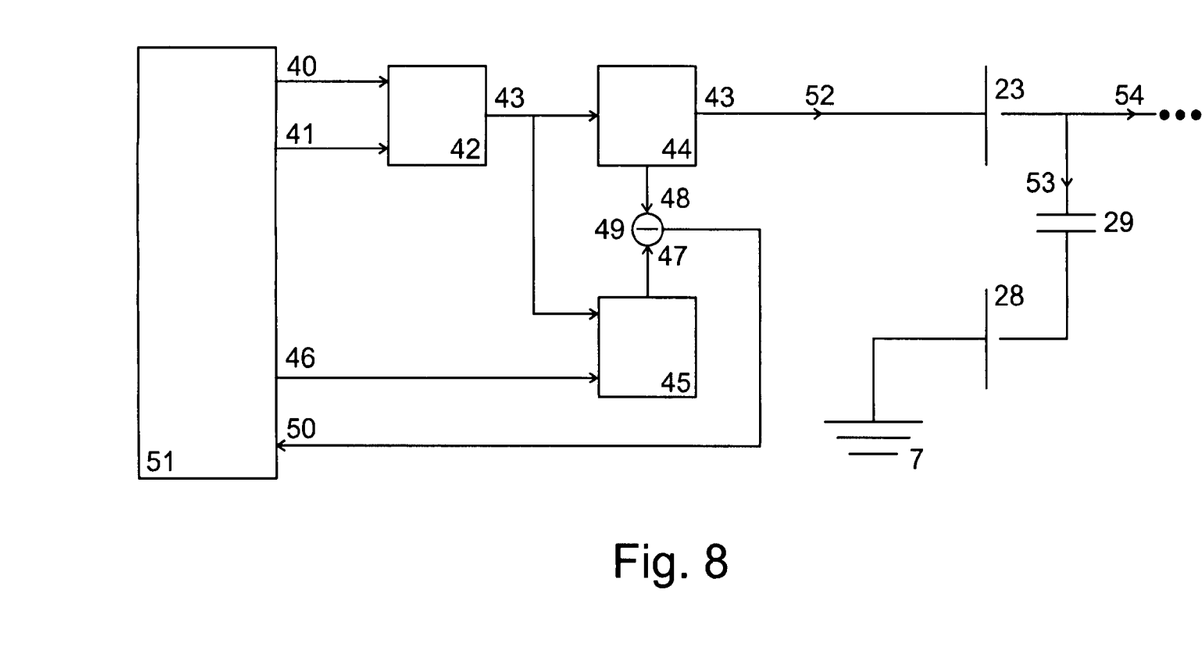
FIG. 8 shows a schematic layout of a constant capacitive offset compensation circuit in the sensing system.

Referring now to FIG. 8, the different reference numerals denote the following features or elements: 7 is the vehicle's GND; 23 is the sensing electrode; 28 is a GND electrode; 29 is the null capacitance between sensing electrode and GND electrode; 40 amplitude control signal; 41 frequency control signal; 42 is the sine voltage generator; 43 is the sine voltage; 44 sensing electrode driver; 45 is multiplier; 46 is the complex transfer function of the null capacitance 29; 47 is an equivalent for the calculated capacitive current through 29; 48 is an equivalent for the capacitive current flowing in 23; 49 is a difference building block; 50 is the difference between 48 and 47; 51 is a control circuitry; 52 is the current necessary to drive 23; 53 is the current flowing through 29; 54 is current flowing towards vehicle GND, e, g, through a passenger.

Via the amplitude and frequency control signals 40 and 41, the control circuitry 51 defines a since wave 43 which is generated by the sine wave generator 42. The sensing electrode driver 44 generates the necessary current 52 to drive to the voltage 43 on the sensing electrode 23. A signal 48 representing said current is fed into the input of a difference building block 49. The current 53, which flows from sensing electrode 23 through capacitance 29 to the GND electrode 28, can be calculated by multiplying voltage 43 with the complex transfer function 46 of the known value of the null capacitance 29. This step respectively the generation of a signal 47 representing said current 53 through 29 is done by block 45. It outputs said signal 47 to the second input of difference building block 49. The output signal 50 of difference building block 49 represents the remaining current 54 which carries the needed information about the occupancy status of the passenger seat and/or environmental influences. This information is extracted by the control unit 51 by e. g. evaluating said signal's amplitude and phase angle in relation to the voltage 43 applied to the sense electrode 23.

The invention claimed is:

1. A capacitive occupant detection system comprising at least one antenna electrode to be arranged in a seat and an evaluation unit operatively coupled to said at least one antenna electrode, wherein said evaluation unit is configured for applying, during operation, an alternating voltage signal to said at least one antenna electrode and for detecting at least one of an amplitude or a phase of a displacement current flowing from said at least one antenna electrode towards ground, and wherein said antenna electrode comprises an antenna electrode conductor and at least one dedicated ground electrode, said ground electrode being arranged at a predetermined distance of said antenna electrode conductor and extending along said antenna electrode conductor.

2. The capacitive occupant detection system as claimed in claim 1, wherein said evaluation unit further comprises circuitry for compensating a capacitive current flowing from said antenna electrode conductor to said at least one dedicated ground electrode.

3. The capacitive occupant detection system as claimed in claim 1, wherein said antenna electrode conductor comprises at least one of a conductive wire or a conductive trace applied on a carrier material.

4. An assembly of a seat heater and a capacitive occupant detection system according to claim 1, wherein said seat heater comprises at least one heater conductor to be arranged in a seat and wherein said seat heater and said capacitive occupant detection system are arranged in said seat in such a way, that said dedicated ground electrode is arranged between said heater conductor and said antenna electrode conductor.

5. The assembly of a seat heater and a capacitive occupant detection system as claimed in claim 4, wherein said heater conductor comprises at least one of a conductive wire or a conductive trace applied on a carrier material.

6. The assembly of a seat heater and a capacitive occupant detection system as claimed in claim 4, wherein said heater conductor and at least one of said antenna electrode conductor or said dedicated ground electrode are arranged on a common carrier material.

7. The assembly of a seat heater and a capacitive occupant detection system as claimed in claim 4, wherein said evaluation unit further comprises circuitry for compensating a capacitive current flowing from said antenna electrode conductor to said at least one dedicated ground electrode.

8. The assembly of a seat heater and a capacitive occupant detection system as claimed in claim 4, wherein said antenna electrode conductor comprises at least one of a conductive wire or a conductive trace applied on a carrier material.

9. The assembly of a seat heater and a capacitive occupant detection system as claimed in claim 7, wherein said antenna electrode conductor comprises at least one of a conductive wire or a conductive trace applied on a carrier material.

10. The capacitive occupant detection system as claimed in claim 2, wherein said antenna electrode conductor comprises at least one of a conductive wire or a conductive trace applied on a carrier material.

* * * * *